United States Patent [19]
Ettlinger et al.

[11] Patent Number: 5,711,797
[45] Date of Patent: Jan. 27, 1998

[54] SILANIZED SILICIC ACIDS

[75] Inventors: Manfred Ettlinger, Karlstein; Dieter Kerner, Hanau; Jürgen Meyer, Rheinfelden, all of Germany

[73] Assignee: Degussa Aktiengesellschaft, Frankfurt, Germany

[21] Appl. No.: 831,947

[22] Filed: Apr. 2, 1997

Related U.S. Application Data

[63] Continuation of Ser. No. 731,023, Oct. 9, 1996, Pat. No. 5,665,156, which is a continuation of Ser. No. 379,694, Jan. 27, 1995, abandoned.

Foreign Application Priority Data

Jan. 27, 1994 [DE] Germany .................. 44 02 370.7

[51] Int. Cl.$^6$ ........................................ C09C 1/30
[52] U.S. Cl. ........................................ 106/287.14
[58] Field of Search ........................ 106/287.14

[56] References Cited

FOREIGN PATENT DOCUMENTS

| | | |
|---|---|---|
| 0216047 | 4/1987 | European Pat. Off. . |
| 0475132 | 3/1992 | European Pat. Off. . |
| 2107082 | 8/1971 | Germany . |
| 62-143908 | 6/1987 | Japan . |

OTHER PUBLICATIONS

4029 World Surface Coatings Abstracts, 64(1991) Jan., No. 583, Head. Hill Hall, GB, 91/00002.

Meng-Jiao Wang and Siegfried Wolff, Filler-Elastomer Interactions . . . Silicas, pp. 715-735, no date avail.

*Primary Examiner*—David Brunsman
*Attorney, Agent, or Firm*—Cushman Darby & Cushman IP Group of Pillsbury Madison & Sutro LLP

[57] ABSTRACT

The silanized, pyrogenically prepared silicic acids are prepared by treating pyrogenically prepared silicic acids with an organosilane selected from the group $(RO)_3SiC_nH_{2n+1}$, in which n—from 10 to 18 and R stands for an alkyl.

4 Claims, No Drawings

SILANIZED SILICIC ACIDS

This is a continuation of application Ser. No. 08/731,023, filed Oct. 9, 1996, now U.S. Pat. No. 5,665,156, which is an FWC of Ser. No. 08/379,694 filed Jan. 27, 1995, now abandoned.

FIELD OF THE INVENTION

The invention relates to silanized silicic acids, the process for preparing them, and their use as a thickening agent.

BACKGROUND OF THE INVENTION

It is known to produce a silanized, pyrogenically made silicic acid by treating the pyrogenically made silicic acid with dimethyldichorosilane (Publish, Examined German Patent Application DE-AS 11 63 784).

Pyrogenically made silicic acids are also known that carry chemically bound —$SiC_8H_{17}$ groups, trimethylsilyl groups, or polydimethylsiloxane groups on their surface (Schriftenreihe Pigmente [Publication Series, "Pigments"] No. 11, page 15, August 1991 Edition).

The subject of the invention is silanized, pyrogenically prepared silicic acids, which are characterized in that the pyrogenically prepared silicic acids are treated with a compound selected from the group $(RO)_3SiC_nH_{2n+1}$, where n=from 10 to 18 and R stands for an alkyl, such as methyl, ethyl, or the like.

A silicic acid prepared by high-temperature hydrolytic means from $SiCl_4+H_2$ and $O_2$ can be used as the pyrogenically prepared silicic acid.

In particular, a temperature-hydrolytically prepared silicic acid can be used that has the following physical-chemical specifications:

Pyrogenic silicic acids of this kind are known. They are described in the following literature, among other sources:

Winnacker-Küchler, Chemische Technologie [Chemical Technology], Vol. 3 (1983), 4th Ed., page 77, and Ullmanns Encyklopädie der technischen Chemie [Ullmann's Encyclopedia of Industrial Chemistry], 4th Ed. (1982), Vol. 21, p. 462.

The pyrogenically prepared silicic acids are treated with a compound selected from the group $(RO)_3SiC_nH_{2n+1}$, where n=from 10 to 18 and R stands for an alkyl, such as methyl, ethyl, or the like.

In particular, the following compounds can be used:

Silane I: $(CH_3O)_3SiC_{16}H_{33}$ (hexadecyltrimethoxysilane)

Silane II: $(CH_3O)_3SiC_{18}H_{37}$ (octadecyltrimethoxysilane)

The silicic acids according to the invention can be prepared in that the pyrogenically prepared silicic acids are placed in a mixer, and while being mixed intensively the silicic acids are sprayed, optionally first with water and then with the compound (organosilane) selected from the group $(RO)_3SiC_nH_{2n+1}$, mixing is continued for from 15 to 30 minutes, and then temperature stabilization is done at a temperature of from 100° to 160° C. over a period of time from 1 to 3 h.

The water used may be acidified with an acid, such as hydrochloric acid, to a pH value of from 7 to 1.

The organosilane used can be dissolved in a solvent, such as ethanol.

The temperature stabilization can be carried out in a protective gas atmosphere, for instance in nitrogen.

The pyrogenically prepared silicic acids, silanized with silane I, according to the invention have the physical-chemical specifications listed in Table 2:

TABLE 1

|  | AEROSIL 90 | AEROSIL 130 | AEROSIL 150 | AEROSIL 200 | AEROSIL 300 | AEROSIL 380 | AEROSIL OX 50 | AEROSIL TT 600 |
|---|---|---|---|---|---|---|---|---|
| Behavior with respect to water |  |  |  | hydrophilic |  |  |  |  |
| Appearance |  |  |  | loose white powder |  |  |  |  |
| Surface area in accordance with BET[1])$m^2$/g | 90 ± 15 | 130 ± 25 | 150 ± 15 | 200 ± 25 | 300 ± 30 | 380 ± 30 | 50 ± 15 | 200 ± 50 |
| Mean size of the primary particles, in nm | 20 | 16 | 14 | 12 | 7 | 7 | 40 | 40 |
| Stamping density[2]) | ca. 80 | ca. 50 | ca. 50 | ca. 50 | ca. 50 | ca. 50 | ca. 130 | ca. 60 |
| Normal goods g/l | — | ca. 120 | ca. 120 | ca. 120 | ca. 120 | ca. 120 | — | — |
| Compacted goods g/l (Additive "V") |  |  |  |  |  |  |  |  |
| Drying loss[3]) (2 hours at 1000° C.) % Upon leaving manufacturing plant | <1.0 | <1.5 | <0.5[9]) | <1.5 | <1.5 | <1.5 | <1.5 | <2.5 |
| Annealing loss[4])[7]) % (2 hours at 1000° C.) | <1 | <1 | <1 | <1 | <2 | <2.5 | <1 | <2.5 |
| pH value[5]) (in 4% aqueous dispersion) | 3.6–4.5 | 3.6–4.3 | 3.6–4.3 | 3.6–4.3 | 3.6–4.3 | 3.6–4.3 | 3.8–4.8 | 3.6–4.5 |
| $SiO_2$[8]) % | >99.8 | >99.8 | >99.8 | >99.8 | >99.8 | >99.8 | >99.8 | >99.8 |
| $Al_2O_3$[8]) % | <0.05 | <0.05 | <0.05 | <0.05 | <0.05 | <0.05 | <0.08 | <0.05 |
| $Fe_2O_3$[8]) % | <0.003 | <0.003 | <0.003 | <0.003 | <0.003 | <0.003 | <0.01 | <0.003 |
| $TiO_2$[8]) % | <0.03 | <0.03 | <0.03 | <0.03 | <0.03 | <0.03 | <0.03 | <0.03 |
| HCl[8])[9]) % | <0.025 | <0.025 | <0.025 | <0.025 | <0.025 | <0.025 | <0.025 | <0.025 |
| Screen residues[6]) (Per Mocker, 45 μm) | <0.05 | <0.05 | <0.05 | <0.05 | <0.05 | <0.05 | <0.2 | <0.05 |

1) in reliance on DIN 86131
2) in reliance on DIN ISO 787/XI, JIS K 5101/18 (unscreened)
3) in reliance on DIN ISO 787/II, ASTM D 280, JIS K 5101/21
4) in reliance on DIN 55 921, ASTM D 1208, JIS K 5101/23
5) in reliance on DIN ISO 787/IX, ASTM D 1208, JIS K 5101/24
6) in DIN ISO 787/XVIII, JIS K 5101/20
7) referred to the 2 hours at 105° C. of dried substance
8) referred to the 2 hours at 1000° C. of the annealed substance
9) HCl-content is a component of the annealing loss

TABLE 2

| E duct | A 90 | A 130 | A 150 | A 200 | A 300 | A 380 | OX 50 | TT 6000 |
|---|---|---|---|---|---|---|---|---|
| Mean size of the primary particles [nm] | 20 | 16 | 14 | 12 | 7 | 7 | 40 | 40 |
| Surface area per BET [$m^2$/g] | 40–90 | 60–130 | 75–150 | 100–200 | 150–300 | 200–380 | 20–50 | 100–250 |
| Stamp density [g/l] | 40–140 | 40–140 | 40–140 | 40–140 | 40–140 | 40–140 | 40–140 | 40–140 |
| Drying loss [%] | <2 | <2 | <2 | <2 | <2 | <2 | <2 | <2 |
| Annealing loss [%] | 0.1–10 | 0.1–10 | 0.1–10 | 0.5–15 | 0.5–20 | 0.5–25 | 0.1–10 | 0.5–20 |
| Carbon Content [%] | 0.1–10 | 0.1–10 | 0.1–10 | 0.5–15 | 0.5–20 | 0.5–25 | 0.1–10 | 0.5–20 |
| pH Value | 3.5–5.5 | 3.5–5.5 | 3.5–5.5 | 3.5–5.5 | 3.5–5.5 | 3.5–5.5 | 3.5–5.5 | 3.5–5.5 |

The silicic acids according to the invention can be employed as thickening agents in liquids, such as water-dilutable paints, and resins such as epoxy resins. The silicic acids according to the invention can also be employed in silicon rubber, rubber, cosmetic articles, toner powders, and as agents for improving pourability and also as reinforcing fillers.

EXAMPLES

The pyrogenically prepared silicic acids employed have the physical-chemical specifications listed in table 1.

As organosilanes, the following compounds of the general formula $(RO)_3SiC_nH_{2n+1}$ are used:

(Silane I) ($CH_3O)_3SiC_{16}H_{33}$ (Silane II) $(CH_3O)_3SiC_{18}H_{37}$

The silicic acid is placed in a mixer and sprayed first with water and then with organosilane, while being mixed intensively.

After the spraying has ended, further mixing continues for from 15 to 30 minutes, and then temperature stabilization is done for from 1 to 3 h at 100° to 160° C. The temperature stabilization may also be done in a protective gas, such as nitrogen.

The various reaction conditions may be learned from table 3.

The physical-chemical specifications of the silanized silicic acids obtained are listed in Tables 3–4.

The thickening action was tested for the silicic acids prepared according to the invention. As the model system, a mixture of propanol and water in a ratio of 1:1 was chosen, with 150 g of starting materials and 7.5 g of silicic acid by weight (5 weight %). Dispersion was done for 5 minutes at 2500 rpm with dissolver and measured with a Brookfield RVT viscometer (spindle 4):

| Example | System or silicic acid | Viscosity |
|---|---|---|
| 8 | propanol/water 1:1 | 80 |
| 9 | Aerosil 200 | 200 |
| 10 | per example 3 | 400 |
| 11 | per example 4 | 14000 |
| 12 | per example 5 | 9800 |
| 13 | per example 6 | 800 |
| 14 | per example 7 | 400 |

It can be seen that the silanized silicic acids according to the invention, in terms of thickening, are superior to the untreated starting silicic acid A 200.

What is claimed is:

1. Silanized, pyrogenically prepared silicic acids, produced by the process characterized in that the pyrogenically prepared silicic acids are placed in a mixer, and while being mixed the silicic acids are sprayed, optionally first with water and then with the compound $(RO)_3SiC_nH_{2n+1}$, where n=from 10 to 18 and R stands for an alkyl, with the proviso that the compound is not stearyltrimethoxysilane, and mixing is continued for from 15 to 30 minutes, and then

TABLE 3

| Example | Aerosil | Silane | Amount of Silane (g/100 g Aerosil) | Amount of Water (/100 g Aerosil) | Amound of Ethanol (g/100 g Aerosil) | Temp. Stabilization Time (h) | Temp. Stabilization Temp. (°C.) |
|---|---|---|---|---|---|---|---|
| 1 | A200 | Silane II | 15 | 0 | 0 | 2 | 120 |
| 2 | A300 | Silane I | 1 | 0 | 9 | 2 | 120 |
| 3 | A200 | Silane I | 2.5 | 0 | 0 | 2 | 140 |
| 4 | A200 | Silane I | 20 | 5 | 0 | 2 | 140 |
| 5 | A200 | Silane I | 10 | 2.5 | 0 | 2 | 140 |
| 6 | A200 | Silane I | 5 | 1.25 | 0 | 2 | 140 |
| 7 | A200 | Silane I | 2.5 | 1.25 | 0 | 2 | 140 |

TABLE 4

| Example | Valve | Stamp density (g/l) | Carbon content (%) | Surface area ($m^2$/g) | Drying loss (%) | Annealing loss (%) |
|---|---|---|---|---|---|---|
| 1 | 4.8 | 52 | 7.9 | 127 | 0.5 | 5.2 |
| 2 | 4.3 | 50 | 1.3 | 253 | 0.4 | 1.8 |
| 3 | 4.4 | 49 | 1.7 | 176 | 0.3 | 2.5 |
| 4 | 4.6 | 68 | 10.1 | 116 | 0.6 | 12.7 |
| 5 | 4.5 | 72 | 5.7 | 144 | 0.6 | 7.1 |
| 6 | 4.7 | 52 | 2.6 | 167 | 0.6 | 3.4 |
| 7 | 4.5 | 51 | 1.9 | 171 | 0.7 | 2.5 | temperature stabilization is done at a temperature of from 100° to 160° C. over a period of time from 1 to 3 h.

2. Silanized, pyrogenically prepared silicic acids of claim 1, characterized in that the compound is hexadecyltrimethoxysilane.

3. Silanized, pyrogenically prepared silicic acids of claim 1, characterized in that the compound is octadecyltrimethoxysilane.

4. A process for preparing silanized, pyrogenically prepared silicic acids, characterized in that pyrogenically prepared silicic acids are placed in a mixer, and while being mixed the silicic acids are sprayed, optionally first with water and then with the compound $(RO)_3SiC_nH_{2n+1}$, mixing is continued for from 15 to 30 minutes, and then temperature stabilization is done at a temperature of from 100° to 160° C. over a period of time from 1 to 3 h.

* * * * *